(12) United States Patent
Asogawa

(10) Patent No.: US 11,199,527 B2
(45) Date of Patent: Dec. 14, 2021

(54) MICROTUBE

(71) Applicant: NEC CORPORATION, Tokyo (JP)

(72) Inventor: Minoru Asogawa, Tokyo (JP)

(73) Assignee: NEC CORPORATION, Tokyo (JP)

(*) Notice: Subject to any disclaimer, the term of this patent is extended or adjusted under 35 U.S.C. 154(b) by 265 days.

(21) Appl. No.: 16/498,164

(22) PCT Filed: Mar. 27, 2018

(86) PCT No.: PCT/JP2018/012339
§ 371 (c)(1),
(2) Date: Sep. 26, 2019

(87) PCT Pub. No.: WO2018/181268
PCT Pub. Date: Oct. 4, 2018

(65) Prior Publication Data
US 2020/0025731 A1    Jan. 23, 2020

(30) Foreign Application Priority Data

Mar. 28, 2017 (JP) .............................. JP2017-062288

(51) Int. Cl.
*G01N 30/91* (2006.01)
*B01L 3/00* (2006.01)
*C12Q 1/686* (2018.01)
*G01N 33/543* (2006.01)
*G01N 35/02* (2006.01)

(52) U.S. Cl.
CPC ............ *G01N 30/91* (2013.01); *B01L 3/5082* (2013.01); *C12Q 1/686* (2013.01); *G01N 33/543* (2013.01); *G01N 35/02* (2013.01); *B01L 2200/027* (2013.01); *B01L 2400/0406* (2013.01)

(58) Field of Classification Search
CPC ......... B01L 2200/027; B01L 2300/042; B01L 2300/047; B01L 2300/0663; B01L 2400/0406; B01L 3/502; B01L 3/5082; B01L 3/50825; C12M 1/00; C12Q 1/686;
(Continued)

(56) References Cited

U.S. PATENT DOCUMENTS 6,068,978 A    5/2000  Zaun et al.
6,153,425 A   11/2000  Kozwich et al.
(Continued)

FOREIGN PATENT DOCUMENTS

CN      203241416       * 10/2013  ............. G01N 33/52
CN      203241416 U      10/2013
(Continued)

OTHER PUBLICATIONS

Translation to English of CN 203241416 by Zhou et al (Year: 2013).*
(Continued)

*Primary Examiner* — Jennifer Wecker
*Assistant Examiner* — Jonathan Bortoli
(74) *Attorney, Agent, or Firm* — Sughrue Mion, PLLC

(57) ABSTRACT

A microtube comprises a sample receptor, a lid and a strip storage storing a chromatography strip. The chromatography strip is stored in a hollow part of the strip storage. The hollow part of the strip storage and an inner space of the sample receptor may be communicated in a closed condition under a state where the sample receptor and the lid are engaged.

9 Claims, 6 Drawing Sheets

(58) Field of Classification Search
CPC ........ G01N 1/00; G01N 30/91; G01N 33/543; G01N 35/02
See application file for complete search history.

(56) References Cited

U.S. PATENT DOCUMENTS

| | | |
|---|---|---|
| 6,649,378 B1 | 11/2003 | Kozwich et al. |
| 2015/0050720 A1 | 2/2015 | Mendoza Montero et al. |

FOREIGN PATENT DOCUMENTS

| | | |
|---|---|---|
| JP | 07-270410 A | 10/1995 |
| JP | 09-504428 A | 5/1997 |
| JP | 2002-532059 A | 10/2002 |
| JP | 2007-292540 A | 11/2007 |
| JP | 2015-512250 A | 4/2015 |
| JP | 2015-230280 A | 12/2015 |

OTHER PUBLICATIONS

International Search Report for PCT/JP2018/012339 dated Jun. 19, 2018 [PCT/ISA/210].

* cited by examiner

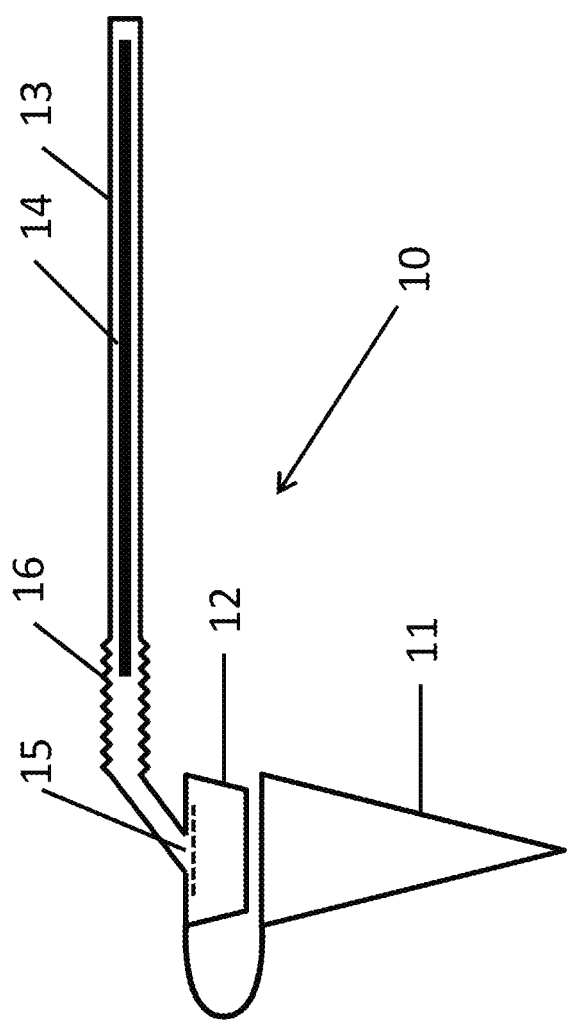
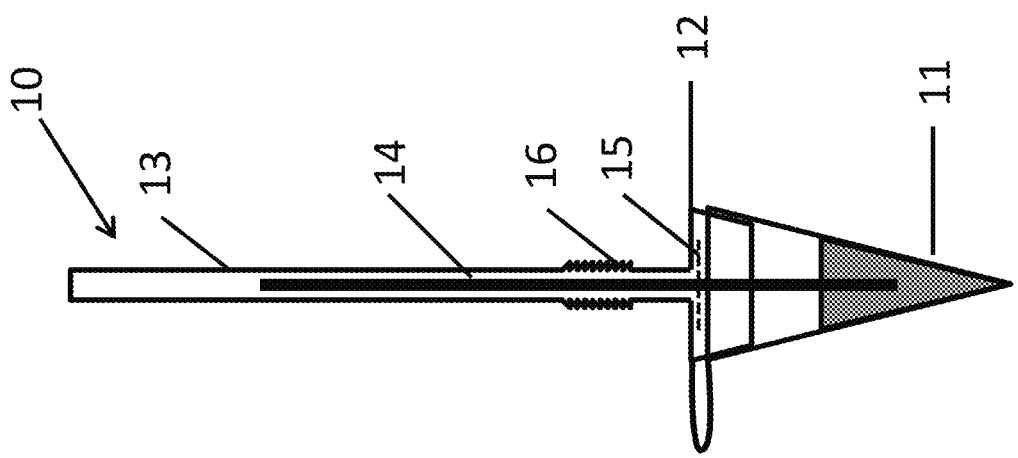
FIG. 2A
FIG. 2B

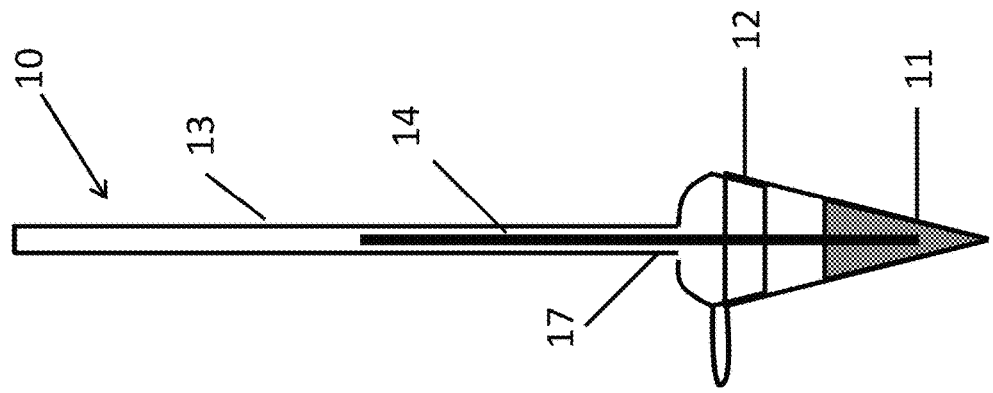
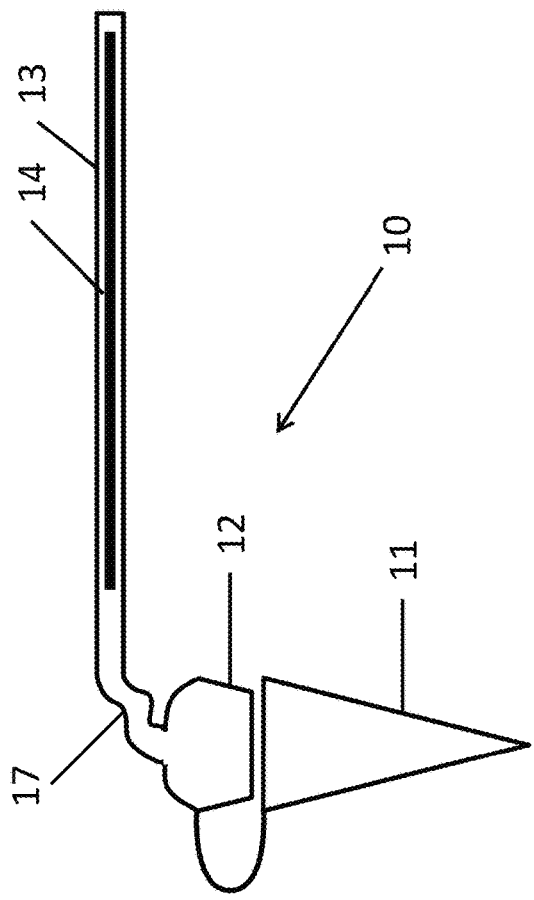
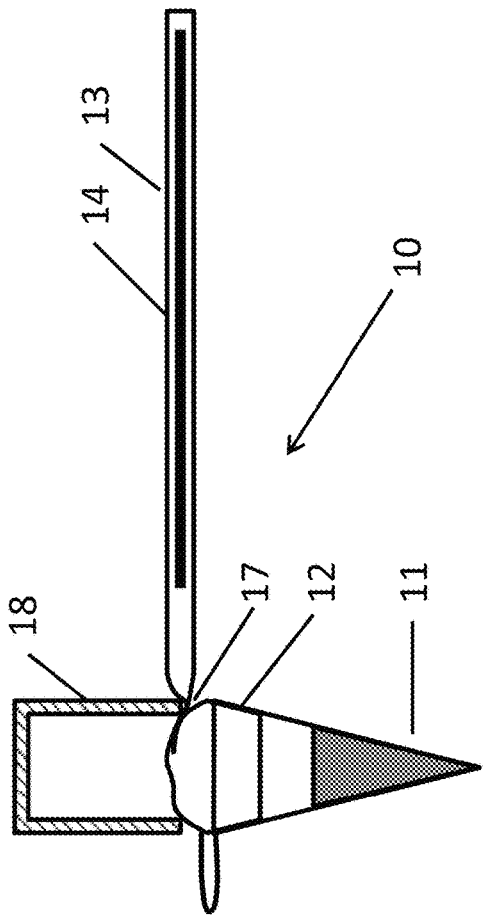

ent contents
MICROTUBE

CROSS-REFERENCE TO RELATED APPLICATION

This application is a National Stage of International Application No. PCT/JP2018/012339 filed Mar. 27, 2019, claiming priority from JP Patent Application No. 2017-062288 filed in Japan on Mar. 28, 2017, the entire contents thereof being incorporated by reference into the present application.

FIELD

The present invention relates a microtube, particularly to a microtube for executing a biochemical reaction.

BACKGROUND

For example, there is a microtube for executing a biochemical reaction, such as PCR (polymerase chain reaction). In addition, a technology for analyzing a result of a biochemical reaction has been established with a chromatography strip, such as a lateral flow strip (Patent Literature (PTL) 1).

PTL 1: JP Patent Application Publication JP 2015-230280A

SUMMARY

The following analysis has been made according to a view of the present invention. Herein, the disclosure of the Prior Art Literature above is incorporated into this application by reference thereto.

There is a situation where a sample, for example, cells and blood, is subjected to direct PCR for examination of virus infection. In a case where PCR result is analyzed with a chromatography strip, such as that disclosed in Patent Literature 1 above, an operator uncaps a microtube for applying the chromatography strip to sample solution, for example, as illustrated in FIG. 6. At that time, the microtube has a possibility to include remaining sample infected by the virus, thus the operator is required to care about secondary infection due to splash of the sample solution and the like.

Therefore, it is a purpose of the present invention to provide a microtube with which a risk of secondary infection may be reduced.

According to a first aspect of the present invention, there is provided a microtube comprising a sample receptor, a lid and a strip storage storing a chromatography strip, wherein the chromatography strip is stored in a hollow part of the strip storage, the hollow part of the strip storage and an inner space of the sample receptor may be communicated in a closed condition under a state where the sample receptor and the lid are engaged.

According to the first aspect of the present invention, there is provided a microtube with which a risk of secondary infection may be reduced.

BRIEF DESCRIPTION OF THE DRAWINGS

FIG. 2A-FIG. 2B are exemplary views of a microtube 10 of a first exemplary embodiment.

FIG. 3A-FIG. 3C are an exemplary view of a microtube 10 of a second exemplary embodiment.

PREFERRED MODES

Figure 1C:
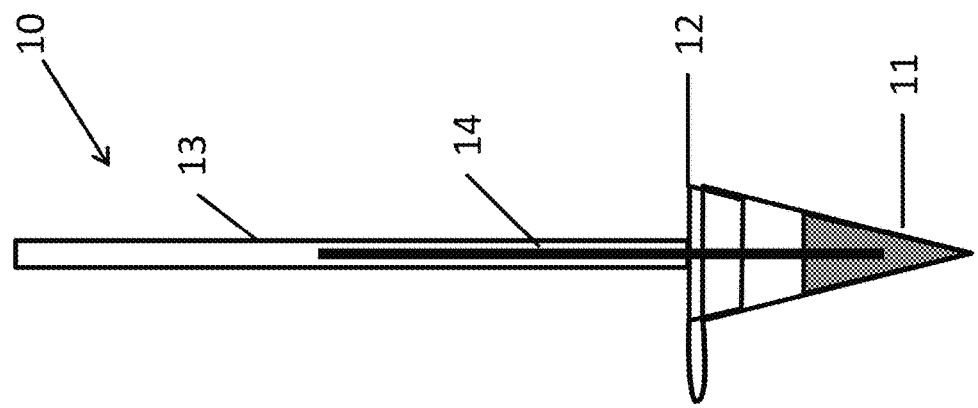
FIG. 1A-FIG. 1C are explanatory views of a schema of a microtube 10 of one exemplary embodiment.

Preferable exemplary embodiments of the present invention will be explained with reference to drawings. Herein, reference signs in the following description are expediently attached to each element as an explanatory aid for understanding, but not for limitation of the present invention to an illustrated configuration.

A microtube 10 comprises a sample receptor 11, a lid 12 and a strip storage 13. A chromatography strip 14 is stored in a hollow part of the strip storage 13. The hollow part of the strip storage 13 and an inner space of the sample receptor 11 may be communicated in a closed state under a situation where the sample receptor and the lid has been engaged.

Figure 1A:
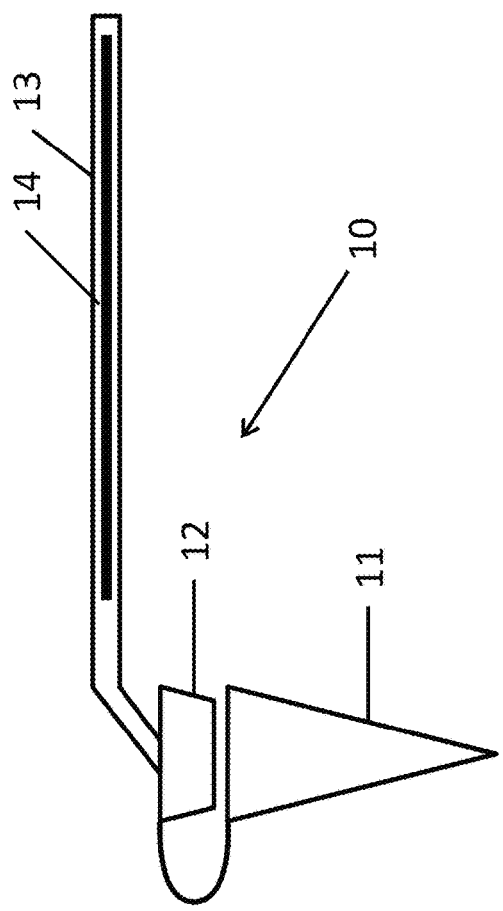
Figure 1B:
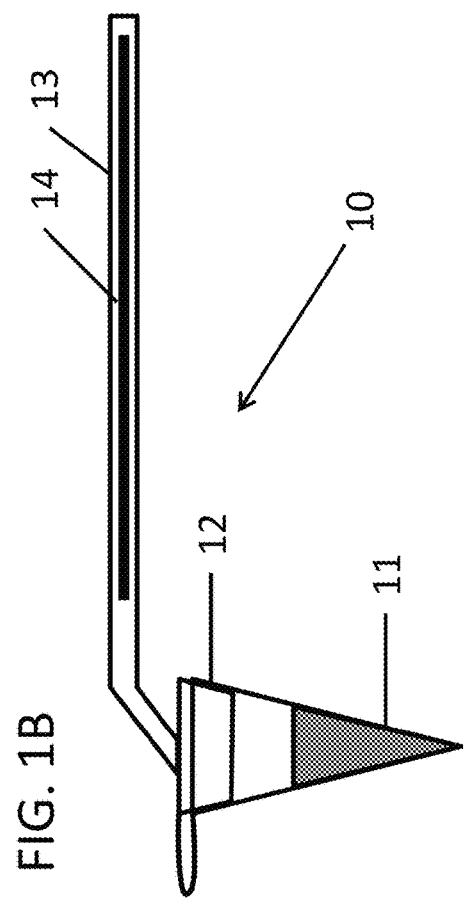

A concrete example will be explained. The strip storage 13 is jointed with the lid 12 at its top as illustrated in FIG. 1A. A biochemical reaction for sample solution in the sample receptor 11, such as PCR (polymerase chain reaction), is executed under a state where the sample receptor 11 and the lid 12 has been engaged as illustrated in FIG. 1B. Under such state, the hollow part of the strip storage 13 and the inner space of the sample receptor 11 are communicated in a closed state. Therefore, after completion of the biochemical reaction, the chromatography strip 14 may be inserted into the sample receptor 11 while keeping the closed state of the inner space of the sample receptor 11 as shown in FIG. 1C. Herein, the chromatography strip 14 may fall into the sample receptor 11 with gravity force or may be pushed into the sample receptor 11 by compressing the strip storage 13.

That is, in the microtube 10 above, when the sample solution is applied to the chromatography strip 14, it is not required to disengage the lid 12, thus a risk of secondary infection due to splash of the sample solution and the like may be reduced.

First Exemplary Embodiment

In a microtube 10 of a first exemplary embodiment, the lid 12 and the strip storage 13 have an integrated configuration, where the chromatography strip 14 is enclosed in the hollow part of the strip storage 13. For example, as illustrated in FIG. 2A, the lid 12 and the strip storage 13 have an integrated configuration made of polypropylene and the like, and the lid 12 is provided with a hole part at the center thereof, which will become an opening part for the strip storage 13. The hole part is covered with a thin film 15. Thus, the hollow part of the strip storage 13 is sealed in a state storing the chromatography strip 14. The strip storage 13 has a bellows section 16, thus it is stretchable and contractable.

After completion of the biochemical reaction, the hollow part of the strip storage 13 and the inner space of the sample receptor 11 are brought into communication by breaking through the lid 12 with the chromatography strip 14 under a state where the sample receptor 11 has been engaged with the lid 12. Concretely, as illustrated in FIG. 2B, the bellows section 16 is compressed in axis direction for shortening the strip storage, and then the chromatography strip 14 breaks through the thin film 15. As a result, the hollow part of the strip storage 13 and the inner space of the sample receptor 11 is brought into communication while keeping the closed state. In such situation, the chromatography strip 14 may be inserted into the inner space of the sample receptor 11 so as to contact to the sample solution.

That is, in the microtube 10 of the first exemplary embodiment, it is not required to disengage the lid 12 upon application of the sample solution to the chromatography strip 14, thus a risk of secondary infection due to splash of the sample solution may be reduced. In addition, the risk of secondary infection may be reduced in a point that the microtube 10 may be disposed as it is after analysis of a result of the biochemical reaction. Furthermore, a work for disengaging the lid 12 may be also omitted.

Herein, in the first exemplary embodiment, it is important that the chromatography strip 14 stored in the hollow part of the strip storage 13 is able to be inserted into the inner space of the sample receptor 11, thus a variety of modified modes may be brought into consideration.

For example, the position of the bellows section 16 may be changed taking a property of the chromatography strip 14 into consideration. That is, in a case where the chromatography strip 14 is used, a result of the biochemical reaction is determined by appearance or absence of a marker (line) on a membrane. Thus, the position of the bellows section 16 may be pertinently changed so that the marker (line) may be visually recognized. In addition, the bellows section 16 itself is not essential. For example, the strip storage 13 may be made of a flexible material, such as rubber, so that it may be shortened. Furthermore, the strip storage 13 may have a thin layer section so as to provide a flexibility for shortening.

The strip storage 13 may be made of a transparent material so that the marker (line) on the membrane is visually recognized, and a monitoring window may also be provided.

In addition, the chromatography strip 14 is desired to have at least a rigidity to an extent capable of breaking through the thin film 15, thus may have various configurations, for example, a plastic bar to which the membrane is attached. Furthermore, the chromatography strip 14 may be provided with a tip end part so as to easily break through the thin film 15. Also, the chromatography strip 14 may be a glass strip on which silica gel etc. are applied, like as a thin layer chromatography.

The thin film 15 may be integrated with the lid 12. That is, the construction of the lid 12 may be modified based on the rigidity of the chromatography strip 14. In addition, the sample receptor 11 may be integrated with the strip storage 13 so that chromatography strip 14 brakes through a wall of the sample receptor 11.

The sample solution is not limited to PCR reaction solution. That is, the sample may be a sample developed by chromatography, thus a nucleic acid sample, protein, carbohydrate chain and the like may be applied. In addition, a container storing solvent for chromatography may be attached to the microtube 10.

Second Exemplary Embodiment

In the microtube 10 of the first exemplary embodiment, the inner space of the sample receptor 11 is separated from the hollow part of the strip storage 13 with the thin film 15 during PCR reaction. Such configuration is for purposes of keeping evaporated sample solution in the inner space of the sample receptor 11 during PCR reaction, and preventing the evaporated sample solution from contacting to the chromatography strip 14. However, the separation of the inner space of the sample receptor 11 from the hollow part of the strip storage 13 may be realized without using the thin film 15. For example, a communication part 17 may be provided, which transiently allows the hollow part of the strip storage 13 to communicate with the inner space of the sample receptor 11.

A concrete example will be explained as second exemplary embodiment. As illustrated in FIG. 3A, the lid 12 of the microtube 10 has an approximately half circle shape so as to be fit with a heat conducting syringe 18 of a heating lid (hot lid) provided on a thermal cycler. A hole part is provided at a center section of the lid 12 of the microtube 10, and a tubular communication part 17 joints the hole part with the strip storage 13. The communication part 17 is made of an elastic material, such as polypropylene. Thereby, as illustrated in FIG. 3B, the communication part 17 is pinched (in other words, pressed) by the heat conducting syringe 18 when the microtube 10 is set on the thermal cycler. As a result, the inner space of the sample receptor 11 is separated from the hollow part of the strip storage 13.

When the microtube 10 is taken from the thermal cycler, the inner space of the sample receptor 11 is brought into communication with the hollow part of the strip storage 13 again. Thus, as illustrated in FIG. 3C, the chromatography strip 14 may be inserted into the inner space of the sample receptor 11 so as to contact to the sample solution.

Herein, in the second exemplary embodiment, it is important that the hollow part of the strip storage 13 is transiently separated from the inner space of the sample receptor 11, thus various modifications may be considered.

For example, the separation of the hollow part of the strip storage 13 from the inner space of the sample receptor 11 may be realized by pinching the communication part 17 with a pinch cock.

In addition, not only for PCR reaction, but also for the other biochemical reactions, it is desired to separate the hollow part of the strip storage 13 from the inner space of the sample receptor 11. That is, the microtube 10 is not limited to a PCR tube.

Third Exemplary Embodiment

In the first and second exemplary embodiments, the cases are explained, where the chromatography strip 14 is inserted into the inner space of the sample receptor 11 so as to contact to sample solution. However, the sample solution may be transferred from the sample receptor 11 to the strip storage 13 so that the sample solution is brought into contact to the chromatography strip 14.

Figure 4:
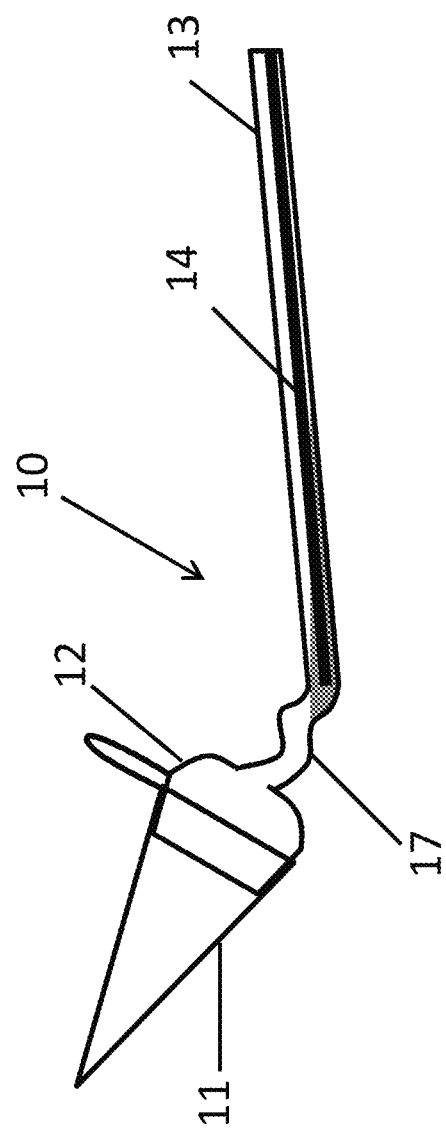
FIG. 4 is an exemplary view of a microtube 10 of a third exemplary embodiment.

A concrete example will be explained as third exemplary embodiment. As illustrated in FIG. 4, the sample receptor 11 may be turned upside down so that the sample solution is transferred to the hollow part of the strip storage 13. Herein, the chromatography strip 14 may be fixed onto the strip storage 13 so that it does not move. In addition, the strip storage 13 may be provided with a liquid chamber (reservoir) part where the sample solution is accumulated.

Fourth Exemplary Embodiment

In the first to third exemplary embodiments, the strip storage 13 is integrated with the microtube 10. However, the strip storage 13 may have a separated configuration from the microtube 10 in a manner capable of being jointed with the microtube 10.

Figure 5B:
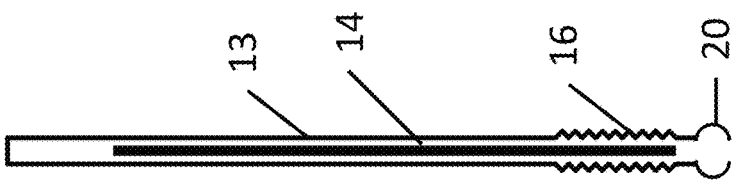
FIG. 5A-5C are an exemplary view of a microtube 10 of a fourth exemplary embodiment.
Figure 5A:
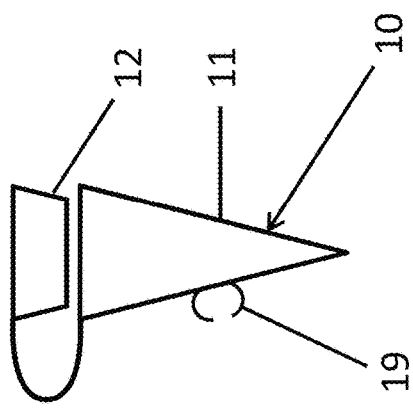
Figure 5C:
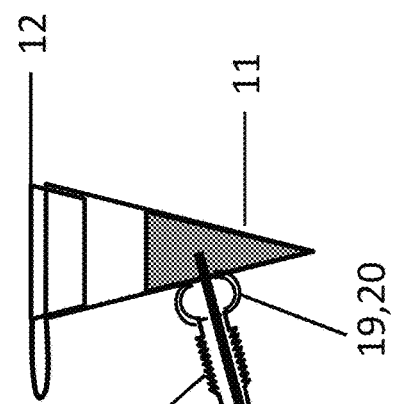
Figure 6:
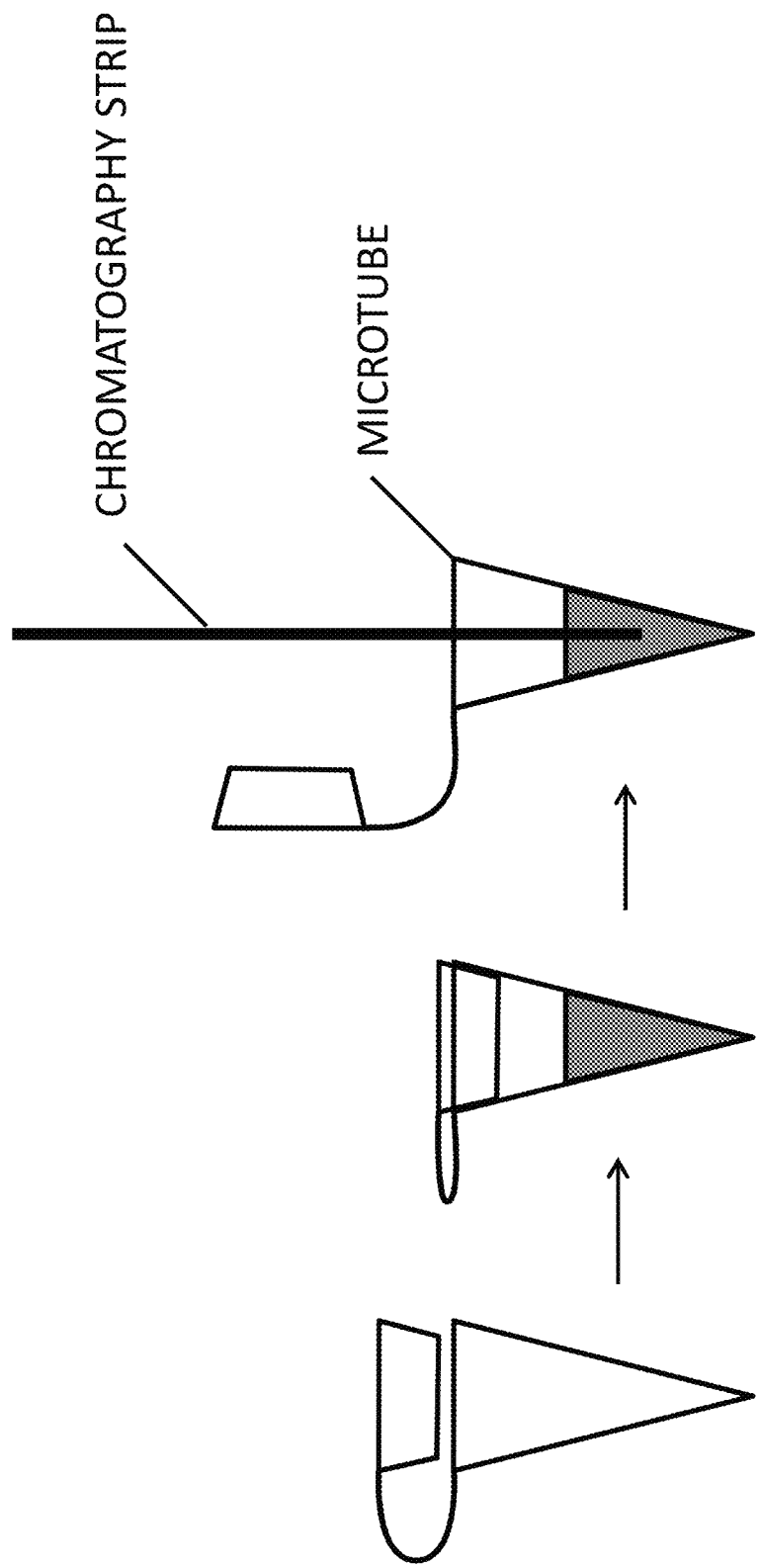
FIG. 6 is an explanatory view for a conventional technology.

A concrete example will be explained as the fourth exemplary embodiment. As illustrated in FIG. 5A, the microtube 10 is integrally provided with a lid 12 and a female joint. In addition, as illustrated in FIG. 5B, the strip storage 13 is provided with a male joint 20 to be jointed with the female joint 19. Furthermore, as illustrated in FIG. 5C, the female joint 19 and the male joint 20 are engaged in a snap fit manner or a screw manner. Herein, when the female joint 19 and the male joint 20 are engaged and then the chromatography strip 14 is inserted into the inner space of the sample receptor 11, the hollow part of the strip storage 13 and the inner space of the sample receptor 11 are brought into communication while keeping a closed state.

As explained above, the strip storage 13 may be a separated configuration from the microtube 10, where it is possible to be jointed to the microtube 10. Therefore, for example, the strip storage 13 may be separated from the microtube 10 during PCR, thus the strip storage 13 does not cause objection upon PCR.

A part or entire of the exemplary embodiments may be described as follows, but not limited thereto.

(Mode 1)

A microtube comprising a sample receptor, a lid and a strip storage storing a chromatography strip, wherein, the chromatography strip is stored in a hollow part of the strip storage, and under a state where the sample receptor and the lid are engaged, the hollow part of the strip storage and an inner space of the sample receptor may be communicated in a closed state.

(Mode 2)

The microtube according to Mode 1, wherein the lid and the strip storage have an integrated configuration, where the chromatography strip is enclosed in the hollow part of the strip storage, the hollow part of the strip storage and the inner space of the sample receptor are brought into communication by breaking through the lid with the chromatography strip under a state where the sample receptor has been engaged with the lid.

(Mode 3)

The microtube according to Mode 2, wherein the strip storage has a bellows section so as to be stretchable and contractable.

(Mode 4)

The microtube according to Mode 1 further comprising a communication part which transiently separates the hollow part of the strip storage from the inner space of the sample receptor.

(Mode 5)

The microtube according to Mode 4, wherein the communication part is made of an elastic material.

(Mode 6)

The microtube according to Mode 4 or 5, wherein the chromatography strip is fixed onto the strip storage.

(Mode 7) The microtube according to Mode 4 or 5, wherein the strip storage comprises a liquid chamber part.

(Mode 8)

A biochemical reaction kit comprising the microtube a according to any one of Modes 1 to 7.

(Mode 9)

A method for analyzing a result of a biochemical reaction with the microtube according to any one of Modes 1 to 7.

Herein, disclosure of the above Patent Literature is incorporated in the present application. The exemplary embodiments or examples may be modified or adjusted within the scope of the entire disclosure of the present invention, inclusive of claims, based on the fundamental technical concept of the invention. In addition, a variety of combinations or selection of elements disclosed herein, inclusive each element in each claim, each element in each example, each element in each drawing etc., may be made within the claims of the present invention. That is, the present invention may cover a wide variety of modifications or corrections that may be made by those skilled in the art in accordance with the entire disclosure of the present invention, inclusive of claims, and the technical concept of the present invention.

REFERENCE SIGNS LIST 10 microtube
11 sample receptor
12 lid
13 strip storage
14 chromatography strip
15 thin film
16 bellows section
17 communication part
18 heat conducting syringe of thermal cycler
19 female joint
20 male joint

The invention claimed is:

1. A microtube comprising a sample receptor, a lid and a strip storage storing a chromatography strip, wherein, the chromatography strip is stored in a hollow part of the strip storage, and under a state where the sample receptor and the lid are engaged, the hollow part of the strip storage and an inner space of the sample receptor may be communicated in a closed state, and further wherein the chromatography strip is enclosed in the hollow part of the strip storage, the hollow part of the strip storage and the inner space of the sample receptor are brought into communication by breaking through the lid with the chromatography strip under a state where the sample receptor has been engaged with the lid.

2. The microtube according to claim 1, wherein the lid and the strip storage have an integrated configuration.

3. The microtube according to claim 2, wherein the strip storage has a bellows section so as to be stretchable and contractable.

4. The microtube according to claim 1 further comprising a communication part which transiently separates the hollow part of the strip storage from the inner space of the sample receptor.

5. The microtube according to claim 4, wherein the communication part is made of an elastic material.

6. The microtube according to claim 4, wherein the chromatography strip is fixed onto the strip storage.

7. The microtube according to claim 4, wherein the strip storage comprises a liquid chamber part.

8. The microtube according to claim 5, wherein the chromatography strip is fixed onto the strip storage.

9. The microtube according to claim 5, wherein the strip storage comprises a liquid chamber part.

* * * * *